United States Patent [19]

Antonini et al.

[11] 4,057,592
[45] * Nov. 8, 1977

[54] OXYCHLORINATION OF ETHYLENE WITH FLUID BED CATALYST

[75] Inventors: Albert Antonini; Philippe Joffre, both of Paris; François Laine, Martiques, all of France

[73] Assignee: Rhone-Poulenc Industries, France

[*] Notice: The portion of the term of this patent subsequent to Sept. 23, 1992, has been disclaimed.

[21] Appl. No.: 535,797

[22] Filed: Dec. 23, 1974

Related U.S. Application Data

[63] Continuation of Ser. No. 144,652, May 18, 1971, abandoned, which is a continuation-in-part of Ser. No. 730,605, May 20, 1968, abandoned.

[51] Int. Cl.$^2$ .............................................. C07C 17/02
[52] U.S. Cl. ............................. 260/659 A; 260/662 A
[58] Field of Search ........... 260/658 R, 659 A, 662 A

[56] References Cited

U.S. PATENT DOCUMENTS

| | | | |
|---|---|---|---|
| 2,846,484 | 8/1958 | Fox | 260/658 R |
| 3,579,597 | 5/1971 | Antonini et al. | 260/658 R |
| 3,642,918 | 2/1972 | Bohl et al. | 260/654 A |
| 3,907,912 | 9/1975 | Antonini et al. | 260/659 A |

FOREIGN PATENT DOCUMENTS

| | | | |
|---|---|---|---|
| 992,847 | 5/1965 | United Kingdom | 260/659 A |

OTHER PUBLICATIONS

Mantell, Adsorption, pp. 44, 45 and 48, (1951).

*Primary Examiner*—C. Davis

[57] ABSTRACT

The process of oxychlorination of ethylene to produce a product in which at least 15 molar per cent of the ethylene is transformed to 1,1,2-trichloroethane and 1,1,2,2-tetrachloroethane along with 1,2-dichloroethane and other more highly chlorinated saturated $C_2$ compounds, the steps of passing a gaseous feed mixture of ethylene, hydrochloric acid and an oxygen-containing gas, with or without additional 1,2-dichloroethane, through a reaction zone at a temperature of 280° to 370° C, using a fluidized bed catalyst, and in which the molar feed ratios of the reactants are $O_2/C_2H_4$ within the range of above 0.9 to 1.5, $HCl/O_2$ within the range of 1.40 to 3.00, $HCl/C_2H_4$ within the range of 2.20 to 3.65, and which, when 1,2-dichloroethane is present in the feed mixture, the latter is present in a molar proportion with respect to ethylene of less than 2.

17 Claims, No Drawings

OXYCHLORINATION OF ETHYLENE WITH FLUID BED CATALYST

This is a continuation of application Ser. No. 144,652, filed May 18, 1971, now abandoned, which in turn was a continuation-in-part of Ser. No. 730,605, filed May 20, 1968, also now abandoned.

This invention relates to the oxychlorination of ethylene in a fluidized catalyst bed to produce 1,2-dichloroethane along with substantial amounts of more highly chlorinated saturated ethanes including 1,1,2-trichloroethane, 1,1,2,2-tetrachlorethane and pentachloroethane.

Processes for production of 1,2-dichloroethane by oxychlorination of ethylene in a fluidized bed catalyst are well known. Such processes have been addressed toward the production of 1,2-dichloroethane as the end product with a view toward minimizing the amounts of other products that might simultaneously be formed therewith. The prior art does not teach processes by which products containing substantial amounts of $C_2$ saturated compounds having a higher degree of chlorination than 1,2-dichloroethane can intentionally be produced, especially without simultaneous parasitic reactions, such as combustion, partial oxidation of ethylene and/or dehydrochlorination reactions which operate to reduce yield and which yield undesirable unsaturated $C_2$ chlorinated compounds which are difficult to separate.

Thus, it is an object of this invention to provide a method and means for oxychlorination of ethylene to yield chlorinated $C_2$ saturated compounds containing substantial proportions of 1,1,2-trichloroethane, 1,1,2,2-tetrachloroethane and pentachloroethane in addition to 1,2-dichloroethane, in which the sum of the 1,1,2-trichloroethane and the 1,1,2,2-tetrachloroethane is at least 15 molar percent of the transformed ethylene and preferably 20 to 40 molar percent of the transformed ethylene. The 1,1,2-trichloroethane and the 1,1,2,2-tetrachloroethane represent commercially valuable compounds which fine a number of uses when used alone or which can be used as raw materials in the manufacture of vinylidene chloride, cis-dichloroethylene and trans-dichloroethylene and trichloroethylenes.

Applicants have achieved the aforementioned objectives with high conversion rate of ethylene and a minimum amount of parasitic reactions such as less than 5 molar percent and preferably less than 2 molar percent combustion and less than 3 molar percent and preferably less than 2 molar percent dehydrochlorination by careful regulation of the feed ratios of reactants, including ethylene, hydrochloric acid and oxygen and careful control of reaction temperature as well as others of the reaction conditions.

A further object of this invention resides in the combination of conditions which includes a catalytic system that makes use of a fluid bed, a well-defined reaction temperature as well as a feed rate of reactants, particularly with respect to the ratio of $O_2/C_2H_4$.

In accordance with the oxychlorination process of this invention, a gaseous mixture of ethylene, HCl and an oxygen-containing gas, preferably air, is passed through a reaction zone maintained at a reaction temperature within the range of 280° to 370° C, and preferably 290° to 340° C at a molar feed rate of ethylene per hour per liter of catalyst of 0.2 to 16 and preferably 0.7 to 8, with the catalyst being maintained in the reaction zone in the form of a fluid bed.

Conversion rates in excess of 80% HCl conversion and combustion rates of ethylene of less than 5% are achieved when the gaseous material making up the reaction mixture is advanced through the reaction zone in the molar ratios of $O_2/C_2H_4$ within the range of above 0.9 to 1.5, $HCl/O_2$ within the range of 1.4 to 3.0, and $HCl/C_2H_4$ within the range of 2.20 to 3.65 with the preferred practice giving a conversion rate in excess of 90% of the HCl conversion and less than about 2% combustion of ethylene when the gaseous material making up the reaction mixture advanced through the reaction zone comprises a molar ratio of $O_2/C_2H_4$ within the range of above 0.9 to 1.20, $HCl/O_2$ within the range of 2.00 to 2.55, and $HCl/C_2H_4$ within the range of 2.50 to 3.25. Air has been used as the source of oxygen in the described reaction but other sources of oxygen or oxygen-enriched air can be used.

With reference to the conditions described, temperature is a factor in the amount of combustion, yields of various valuable chlorinated ethane compounds, which yields are characteristic of the non-selectivity of the reaction, and the amount and type of side reactions. When a temperature in excess of 370° C. is employed, side reactions become excessive and combustion exceeds practical values and an excessive amount of unsaturated compounds are produced. On the other hand, when the temperature is below 280° C., non-selectivity is experienced to a very slight extent, whereby little, if any, of the more highly chlorinated ethane derivatives are produced.

The time of exposure to reaction conditions, or residence time, is, of course, a factor of temperature, velocity of the reaction gases through the reaction zone and catalyst. Under the conditions described, best results are secured at a residence time within the range of 2 to 25 seconds, and it is undesirable to exceed a residence time of 40 seconds.

Similarly, within the described conditions for reaction, some variation in product distribution can be achieved by variations in the reactant ratios. For example, preparation of saturated $C_2$ compounds more highly chlorinated than 1,2-dichloroethane increases with increase in the molar ratio of $O_2/C_2H_4$ in the feed. It has been found further that the amount of side reactions, that is combustion and dehydrochlorination, decreases with increasing ratio of $HCl/O_2$ in the feed, while maintaining constant the ratios of $O_2/C_2H_4$ in the feed. This provides a means within the conditions of the invention which permits an increase in the non-selectivity of the reaction, while decreasing the amount of side reactions.

The applicants have established a correlation between the $O_2/C_2H_4$ and $HCl/O_2$ feed molar ratio, when air is used as gas comprising oxygen. This is to say that by setting beforehand the conversion rate of the ethylene into parasitic burning products ($CO + CO_2$) at an upper limit which must not be exceeded, and which is of 5% and preferably of 2 molar %, the molar ratio $HCl/O_2$ must have values superior or equal to a limit which depends on the $O_2/C_2H_4$ feed molar ratio.

Tables I and II hereafter summarize the correlation established by the applicants:

TABLE I

Lower limit of the HCl/O$_2$ molar ratio as a function of the O$_2$/C$_2$H4 molar ratio for a specified combustion rate limit of C$_2$H4.

| Combustion Limit Rate | 5 | 4 | 3 | 2 |
|---|---|---|---|---|
| O$_2$/C$_2$H4 | 0.91 | 0.91 | 0.91 | 0.91 |
| HCl/O$_2$ ≧ | 2.20 | 2.27 | 2.38 | 2.58 |
| O$_2$/C$_2$H4 | 1.10 | 1.10 | 1.10 | 1.10 |
| HCl/O$_2$ ≧ | 1.85 | 1.91 | 2.02 | 2.20 |
| O$_2$/C$_2$H4 | 1.30 | 1.30 | 1.30 | 1.30 |
| HCl/O$_2$ ≧ | 1.55 | 1.60 | 1.69 | 1.86 |
| O$_2$/C$_2$H4 | 1.50 | 1.50 | 1.50 | 1.50 |
| HCl/O$_2$ ≧ | 1.25 | 1.29 | 1.37 | 1.52 |

TABLE II

Upper limit of the HCl/O$_2$ molar ratio as a function of the O$_2$/C$_2$H4 molar ratio for a specified conversion rate of HCl.

| Conversion Rate of HCl % | 80 | 90 | 92 | 94 | 96 |
|---|---|---|---|---|---|
| O$_2$/C$_2$H4 | 0.91 | 0.91 | 0.91 | 0.91 | 0.91 |
| HCl/O$_2$ ≦ | 3.34 | 2.90 | 2.81 | 2.72 | 2.64 |
| O$_2$/C$_2$H4 | 1.10 | 1.10 | 1.10 | 1.10 | 1.10 |
| HCl/O$_2$ ≦ | 2.95 | 2.56 | 2.48 | 2.40 | 2.32 |
| O$_2$/C$_2$H4 | 1.30 | 1.30 | 1.30 | 1.30 | 1.30 |
| HCl/O$_2$ ≦ | 2.69 | 2.36 | 2.28 | 2.22 | 2.15 |
| O$_2$/C$_2$H4 | 1.50 | 1.50 | 1.50 | 1.50 | 1.50 |
| HCl/O$_2$ ≦ | 2.43 | 2.15 | 2.09 | 2.04 | 1.98 |

Pressure does not have a significant effect on the ratio of components in the product, but it does have effect on productivity with increased productivity being obtained with increase in pressure. It is desirable to carry out the reaction of this invention under a pressure within the range of 1 to 10 bars absolute and preferably 4 to 9 absolute bars. Pressures higher than 10 bars can be used, within the limits of the equipment, but no great advantage is derived from the use of pressures greater than 10 bars.

In accordance with a particular modification of the practice of this invention, the feed may include 1,2-dichloroethane along with the ethylene, hydrochloric acid and oxygen-containing gas for passage together through the catalytic reaction zone with the added 1,2-dichloroethane present in a molar proportion of less than 2 based upon the amount of ethylene.

The catalyst employed for the practice of this invention comprises a catalytic agent deposited on a carrier having an average specific surface greater than 1 m$^2$/g and preferably greater than 10 m$^2$/g. The term "average specific surfaces," as used herein, means that if a series of specimens are taken from different portions of the catalytic mass in order to determine the specific surface area of the carrier in accordance with the B.E.T. method, the results will show a dispersion with the extremes within 25% of the average value.

The catalyst carrier may be preferably formed of synthetic silica-based mixtures containing magnesia, with the average particle size of the carrier preferably being within the range of 20 to 400 microns, and most preferably 40 to 120 microns. Good results have been secured with attapulgite type clays, which consist essentially of silica and magnesia, having an average specific surface within the range of 10 to 160 m$^2$/g and preferably within the range of 60 to 160 m$^2$/g. Very good results have been obtained with a carrier consisting essentially of silica and magnesia having an average specific surface area within the range of 40 to 200 m$^2$/g and preferably 80 to 160 m$^2$/g. The latter exhibits excellent characteristics from the standpoint of fluidization in the fluid bed catalyst.

When the upper limit of the average specific surface area is exceeded, combustion is increased and excessive amounts of catalytic cracking takes place to produce C$_1$ products, as well as chlorinated ethylenic C$_2$ compounds.

Use can be made of conventional catalytic agents such as are formed of at least a compound of a metal selected from the group of alkali metals, alkaline earth metals, bismuth, cadmium, chromium, cobalt, copper, tin, iron, manganese, magnesium, platinum, rare earths, thorium, vanadium, zirconium, zinc, nickel, or mixtures thereof. Preferred catalysts are formed of mixtures of copper and potassium salts (e.g., copper chloride plus potassium chloride).

The following examples are given by way of illustration, but not by way of limitation, of the practice of this invention:

EXAMPLES 1 to 4

The oxychlorination reaction of ethylene is carried out in a reactor in the form of a glass tube having an internal diameter of 65 mm and a height of 1000 mm and externally heated by resistance coils. The lower portion of the tube is provided with a reversed cone filled with glass beads having a diameter of 2 mm for mixing the reactants and to diffuse the gases into the catalytic bed. The height of the catalytic bed, at rest, after fluidization, is 450 mm. The catalyst is prepared by impregnating an attapulgite type clay with an aqueous solution of Cl$_2$Cu, 2 H$_2$O and KCl such that the final content of dry catalyst when measured on the basis of the copper and potassium cations is respectively 8.7% and 4.9% by weight. The average specific surface area of the carrier, measured when the catalyst has been operated under normal operating conditions for about 100 hours of reaction, is about 80 m$^2$/g. The catalytic mass has a grain size distribution (granulometry) ranging from 100 to 315 $\mu$, in which 50% of the mass has a grain size lower than 210 $\mu$.

During the operation, the reactants of ethylene, air and gaseous hydrochloric acid are introduced under absolute pressure of 1.05 bar into the lower portion of the reversed cone section and the reactor is heated by the electrical resistance coils controlled by thermocouples placed between the external wall of the tube and the electrical resistance. The catalytic bed is uniformly maintained at a constant temperature of 325° ± 2° C.

The products of the reaction have a composition which varies as a function of the temperature of the catalytic bed and the feed ratio of the reactants.

The following Table III presents the results of the process of the invention over several thousands of hours of operation without variation in the activity of the catalyst after working for 2500 hours. Table III sets forth a characteristic ratio of the obtained results defined as follows:

$$R = \frac{100\,(X + Y + Z)}{(W + X + Y + Z)}$$

in which W represents the conversion rate of ethylene into 1,2-dichloroethane, X represents the conversion rate of ethylene into 1,1,2-trichloroethane, Y represents the conversion rate of ethylene into 1,1,2,2-tetrachloroethane and Z represents the conversion rate of ethylene into pentachloroethane.

TABLE III

| EXAMPLES No. | | 1 | 2 | 3 | 4 |
|---|---|---|---|---|---|
| Flow rate of $C_2H_4$ mole/h and per liter of catalyst | | 0.97 | 0.96 | 0.95 | 0.98 |
| Molar feed ratio | $HCl/O_2$ | 2.43 | 2.82 | 2.61 | 2.59 |
| | $O_2/C_2H_4$ | 0.95 | 0.96 | 0.97 | 0.94 |
| | $HCl/C_2H_4$ | 2.31 | 2.71 | 2.53 | 2.43 |
| W | | 71.0 | 72.7 | 70.9 | 68.3 |
| X | | 13.9 | 15.5 | 16.4 | 17.4 |
| Y | | 8.1 | 6.7 | 6.8 | 8.5 |
| Z | | 0.6 | 1.0 | 0.7 | 0.6 |
| Conversion rate of $C_2H_4$ into $CO_2$ | | 4.0 | 1.7 | 2.6 | 2.9 |
| Conversion rate of $C_2H_4$ into chlorinated ethylenic by-products | | 1.6 | 1.3 | 1.7 | 1.2 |
| Total conversion rate of reactants molar % | $C_2H_4$ | 98.7 | 99.1 | 99.2 | 99.2 |
| | HCl | 95.5 | 83.9 | 89.0 | 93.8 |
| (W + X + Y + Z) | | 92.6 | 95.9 | 94.8 | 94.8 |
| $R = \frac{100(X + Y + Z)}{(W + X + Y + Z)}$ | | 23.3 | 24.2 | 25.2 | 27.9 |

These results show that a substantial proportion of 1,1,2-trichloroethane and 1,1,2,2-tetrachloroethane can be secured along with 1,2-dichloroethane without excessive combustion or formation of by-products such as vinyl chloride, dichloroethylene, and the like. For instance, Example 4 shows that ethylene is transformed at the rate of 94.8% into a mixture of 1,2-dichloroethane, 1,1,2-trichloroethane, 1,1,2,2-tetrachloroethane and pentachloroethane, the composition of which is as follows:

| 1,2-Dichloroethane | 72.0 molar % i.e., 63.6% by weight |
|---|---|
| 1,1,2-Trichloroethane | 18.35 molar % i.e., 21.9% by weight |
| 1,1,2,2-Tetrachloroethane | 9.0 molar % i.e., 13.2% by weight |
| Pentachloroethane | 0.65 molar % i.e., 1.2% by weight |

The total conversion rate of hydrochloric acid is high since it rises to 93.8 and the formation of by-products and of combustion products is very limited, such as 4.1% of the ethylene.

EXAMPLES 5 to 7

The same apparatus, the same temperature, and the same catalyst were used as in Example 1, but the reactor is fed with a mixture of ethylene, air, gaseous HCl and 1,2-dichloroethane vapors. The mixture is preheated to 80° C to avoid the condensation of 1,2-dichloroethane. The results are set forth in the following Table IV:

TABLE IV

| EXAMPLES NO. | | 5 | 6 | 7 |
|---|---|---|---|---|
| Flow rate of $C_2H_4$ mole/n and per liter of catalyst | | 0.88 | 0.90 | 0.88 |
| Molar feed ratio | $HCl/O_2$ | 2.34 | 2.48 | 2.80 |
| | $O_2/C_2H_4$ | 1.10 | 1.10 | 1.09 |
| | $HCl/C_2H_4$ | 2.57 | 2.73 | 3.09 |
| W | | 66.3 | 64.9 | 68.2 |
| X | | 19.9 | 20.9 | 20.6 |
| Y | | 8.5 | 9.2 | 7.1 |
| Z | | 1.0 | 1.1 | 0.8 |
| Conversion rate of $C_2H_4$ into $CO_2$ | | 2.6 | 1.8 | 1.2 |
| Conversion rate of $C_2H_4$ into chlorinated ethylenic by-products | | 1.6 | 1.6 | 1.5 |
| Total conversion rate of reactants molar % | $C_2H_4$ | 99 | 99.1 | 99.5 |
| | HCl | 88.8 | 87.0 | 76.1 |
| (W + X + Y + Z) | | 95.7 | 96.1 | 96.7 |
| $R = \frac{100(X + Y + Z)}{(W + X + Y + Z)}$ | | 30.7 | 32.5 | 29.4 |

These tests show that the conversion rate of ethylene into 1,1,2-trichloroethane, 1,1,2,2-tetrachloroethane and pentachloroethane can be increased substantially by recycling a part of the product 1,2-dichloroethane since the R ratio rises to 32.5% (Example 6) with a combustion rate relatively low and total conversion rates of $C_2H_4$ and of HCl being relative high. The feed ratio of the reactants $CH_2Cl$-$CH_2Cl/C_2H_4$ in Examples 5, 6 and 7 are respectively 0.28, 0.27 and 0.28. The composition of the collected liquids of Example 6 is as follows:

| - 1,2-Dichloroethane | 67.5 molar %, i.e. 58.5% by wt. |
|---|---|
| - 1,1,2-Trichloroethane | 21.7 molar %, i.e. 25.4% by wt. |
| - 1,1,2,2-Tetrachloroethane | 9.6 molar %, i.e. 14.0% by wt. |
| - Pentachloroethane | 1,2 molar %, i.e. 2.1% by wt. |

EXAMPLE 8

The oxychlorination reaction of ethylene is carried out in the same apparatus and with the same catalyst as in Examples 1 to 4. The temperature of the catalytic bed is maintained at 325° ±2° C.

Table V, hereinafter set forth, summarizes the results obtained. The table also includes a comparative test (Example d) wherein the molar ratio of $HCl/O_2$ is outside the prescribed limits of the invention with all other operational conditions being the same as in Example 8.

It will be noticed from Example d that ethylene is transformed into $CO_2$ at the rate of 13.5 molar percent whereas in Example 8 the rate of formation of $CO_2$ is only 2.8 molar percent. The production of chlorinated ethylenic by-products is 5.2 molar percent of Example d whereas it is only 2.1 molar percent in Example 8. It may also be noted that the conversion rate of ethylene into 1,1,2-trichloroethane is substantially lower in Example d (7.2%) than in Example 8 (14.5%). Similar results are observed for the ratio R which is 14.6% for Example d and 20.1% for Example 8.

TABLE V

| EXAMPLES NO. | | 8 | d |
|---|---|---|---|
| Flow rate of $C_2H_4$ mole/h and per liter of catalyst | | 0.71 | 0.71 |
| Molar feed ratio | $HCl/O_2$ | 1.49 | 1.20 |
| | $O_2/C_2H_4$ | 1.50 | 1.50 |
| | $HCl/C_2H_4$ | 2.24 | 1.80 |
| W | | 75.5 | 65.0 |
| X | | 14.5 | 7.2 |
| Y | | 4.0 | 3.5 |
| Z | | 0.5 | 0.4 |
| Conversion rate of $C_2H_4$ into $CO_2$ | | 2.8 | 13.5 |
| Conversion rate of $C_2H_4$ into chlorinated ethylenic by-products | | 2.1 | 5.2 |
| Total conversion rate of reactants molar % | $C_2H_4$ | 99.4 | 94.8 |
| | HCl | 96.9 | 98.9 |
| (W + X + Y + Z) | | 94.5 | 76.1 |
| $R = \frac{100(X + Y + Z)}{(W + X + Y + Z)}$ | | 20.1 | 14.6 |

EXAMPLES 9 and 10

The oxychlorination of ethylene is carried out in an Inconel (73% Ni alloy) reactor having an internal diameter of 120 mm and a height of 2000 mm and heated externally by an electrical resistance. The lower part of the reactor is provided with a perforated screen having openings of 3 mm in diameter to provide 1.2% of empty space, which screen is employed to distribute the gaseous reactants which have previously been mixed. At its upper portion, a filtration device operates to hold back the catalyst is the same as in Examples 1 to 4, except that the average particle size of said catalyst is of 140 microns instead of 210 microns.

During the operation, ethylene, air and gaseous hydrochloric acid are introduced under an absolute pressure of 7.2 bars into the lower part of the reactor through the perforated screen. The reactor is heated with the external electric resistance regulating the temperature of the external wall of the tube and the electrical resistance. The temperature of the catalytic fluid bed is maintained constant and homogeneous at 330° ± 2° C.

The following Table sets forth the results obtained:

TABLE VI

| EXAMPLES NO. | | 9 | 10 |
|---|---|---|---|
| Flow rate of $C_2H_4$ mole/h and per liter catalyst | | 9.2 | 9.2 |
| Molar feed ratio | $HCl/O_2$ | 2.35 | 1.96 |
| | $O_2/C_2H_4$ | 1.0 | 1.2 |
| | $HCl/C_2H_4$ | 2.35 | 2.35 |
| Temperature ° C. | | 300 | 300 |
| W | | 78.4 | 78.4 |
| X | | 10.5 | 10.5 |
| Y | | 4.6 | 4.5 |
| Z | | 0.33 | 0.35 |
| Conversion rate of $C_2H_4$ into $CO_2$ | | 2.4 | 2.4 |
| Conversion rate of $C_2H_4$ into chlorinated ethylenic products and $C_2H_5Cl$ | | 1.4 | 1.4 |
| Total conversion rate of reactants molar % | $C_2H_4$ | 97.6 | 97.5 |
| | HCl | 88 | 88 |
| (W + X + Y + Z) | | 93.8 | 93.7 |
| R | | 16.1 | 16.0 |

It will be understood that changes may be made in the details of formulation and operation without departing from the spirit of the invention, especially as defined in the following claims.

We claim:

1. A process for the oxychlorination of ethylene to produce a product in which at least 15 mole percent of the ethylene is transformed into 1,1,2-trichloroethane and 1,1,2,2-tetrachloroethane, in which less than 5 mole percent of the ethylene is transformed into combustion products and in which less than 3 mole percent of the ethylene is transformed to unsaturated $C_2$ chlorinated compounds, comprising passing a gaseous feed mixture of ethylene, hydrogen chloride and an oxygen containing gas through a reaction zone maintained at a temperature within the range of 280° to 370° C and containing a fluid bed catalyst comprising an oxychlorination catalyst deposited on a carrier consisting essentially of silica and magnesia having a surface area within the range of 10 to 200 m²/g, in which the molar feed ratios of the reactants are a ratio of $O_2/C_2H_4$ within the range of above 0.9 to 1.5, a ratio of $HCl/O_2$ within the range of 1.40 to 3.0 and a ratio of $HCl/C_2H_4$ within the range of 2.20 to 3.65.

2. A process as defined in claim 1 wherein the carrier is selected from the group consisting of attapulgite clay having a surface area within the range of 10 to 160 m²/g. and a synthetic mixture of silica and magnesia having a surface area within the range of 40 to 200 m²/g.

3. A process for the oxychlorination of ethylene to produce a product in which at least 15 mole percent of the ethylene is transformed into 1,1,2-trichloroethane and 1,1,2,2-tetrachloroethane, in which less than 5 mole percent of the ethylene is transformed into combustion products and in which less than 3 mole percent of the ethylene is transformed to unsaturated $C_2$ chlorinated compounds, comprising passing a gaseous feed mixture of ethylene, hydrogen chloride and air through a reaction zone maintained at a temperature within the range of 280° to 370° C and containing a fluid bed catalyst comprising an oxychlorination catalyst deposited on a carrier consisting essentially of silica and magnesia having a surface area within the range of 10 to 200 m²/g, wherein the feed mixture contains the reactants in a mole ratio of $O_2/C_2H_4$ within the range of above 0.9 to 1.5, a mole ratio of $HCl/O_2$ within the range of 1.40 to 3.0 and a mole ratio of $HCl/C_2H_4$ within the range of 2.20 to 3.65 and the lower limit of the mole ratio of $HCl/O_2$ is correlated with the mole ratio of $O_2/C_2H_4$ to provide a maximum combustion rate in accordance with the following:

| Maximum Combustion Rate (Mole %) | 5 | 4 | 3 | 2 |
|---|---|---|---|---|
| $O_2/C_2H_4$ | 0.91 | 0.91 | 0.91 | 0.91 |
| $HCl/O_2 \geq$ | 2.20 | 2.27 | 2.38 | 2.58 |
| $O_2/C_2H_4$ | 1.10 | 1.10 | 1.10 | 1.10 |
| $HCl/O_2 \geq$ | 1.85 | 1.91 | 2.02 | 2.20 |
| $O_2/C_2H_4$ | 1.30 | 1.30 | 1.30 | 1.30 |
| $HCl/O_2 \geq$ | 1.55 | 1.60 | 1.69 | 1.86 |
| $O_2/C_2H_4$ | 1.50 | 1.50 | 1.50 | 1.50 |
| $HCl/O_2 \geq$ | 1.25 | 1.29 | 1.37 | 1.52 | and the upper limit of the mole ratio of $HCl/O_2$ is correlated with the mole ratio of $O_2/C_2H_4$ to provide an HCl conversion rate in accordance with the following:

| Conversion Rate of HCl (Mole %) | 80 | 90 | 92 | 94 | 96 |
|---|---|---|---|---|---|
| $O_2/C_2H_4$ | 0.91 | 0.91 | 0.91 | 0.91 | 0.91 |
| $HCl/O_2 \leq$ | 3.34 | 2.90 | 2.81 | 2.72 | 2.64 |
| $O_2/C_2H_4$ | 1.10 | 1.10 | 1.10 | 1.10 | 1.10 |
| $HCl/O_2 \leq$ | 2.95 | 2.56 | 2.48 | 2.40 | 2.32 |
| $O_2/C_2H_4$ | 1.30 | 1.30 | 1.30 | 1.30 | 1.30 |
| $HCl/O_2 \leq$ | 2.69 | 2.36 | 2.28 | 2.22 | 2.15 |
| $O_2/C_2H_4$ | 1.50 | 1.50 | 1.50 | 1.50 | 1.50 |
| $HCl/O_2 \leq$ | 2.43 | 2.15 | 2.09 | 2.04 | 1.98 |

4. The process as claimed in claim 3 in which the reactants are present in the feed in the ratio of $O_2/C_2H_4$ within the range of above 0.9 to 1.20, $HCl/O_2$ within the range of 2.00 to 2.55 and $HCl/C_2H_4$ within the range of 2.50 to 3.25.

5. The process as claimed in claim 3 in which the temperature of the reaction zone is maintained within the range of 290° to 340° C.

6. The process as claimed in claim 3 in which the molar feed rate of ethylene is within the range of 0.2 to 16 moles per hour per liter of catalyst.

7. The process as claimed in claim 3 in which the molar feed ratio of ethylene is 0.7 to 8 moles per hour per liter of catalyst.

8. The process as claimed in claim 3 in which the reaction is carried out under a pressure within the range of 1 to 10 absolute bars.

9. The process as claimed in claim 3 in which the reaction is carried out under a pressure within the range of 4 to 9 absolute bars.

10. The process as claimed in claim 3 in which the carrier for the catalyst is an attapulgite clay having an average specific surface area of 10 to 160 m²/g.

11. The process as claimed in claim 3 which the carrier for the catalyst is a synthetic mixture consisting essentially of silica and magnesia having an average specific surface area of 40 to 200 m²/g.

12. The process as claimed in claim 3 in which the reactants have a residence time in the reaction zone of from 2 to 25 seconds.

13. The process as claimed in claim 3 in which the reactants have a residence time in the reaction zone of up to 40 seconds.

14. A process for the oxychlorination of ethylene to produce a product in which at least 15 mole percent of the ethylene is transformed into 1,1,2-trichloroethane and 1,1,2,2-tetrachloroethane, in which less than 5 mole percent of the ethylene is transformed into combustion products and in which less than 3 mole percent of the ethylene is transformed to unsaturated $C_2$ chlorinated compounds, comprising passing a gaseous feed mixture of ethylene, hydrogen chloride and an oxygen containing gas through a reaction zone maintained at a temperature within the range of 280° to 370° C and containing a fluid bed catalyst comprising a copper containing catalyst deposited on a carrier selected from the group consisting of attapulgite clay having a surface area within the range of 10 to 160 m²/g and a synthetic mixture of silica and magnesia having a surface area within the range of 40 to 200 m²/g, in which the molar feed ratios of the reactants are a ratio of $O_2/C_2H_4$ within the range of above 0.9 to 1.5 a ratio of $HCl/O_2$ within the range of 1.40 to 3.0 and a ratio of $HCl/C_2H_4$ within the range of 2.20 to 3.65.

15. A process for the oxychlorination of ethylene to produce a product in which at least 15 mole percent of the ethylene is transformed into 1,1,2-trichloroethane and 1,1,2,2-tetrachloroethane, in which less than 5 mole percent of the ethylene is transformed into combustion products and in which less than 3 mole percent of the ethylene is transformed to unsaturated $C_2$ chlorinated compounds, comprising passing a gaseous feed mixture of ethylene, hydrogen chloride and air through a reaction zone maintained at a temperature within the range of 280° to 370° C and containing a fluid bed catalyst comprising a copper containing catalyst deposited on a carrier selected from the group consisting of attapulgite clay having a surface area within the range of 10 to 160 m²/g and a synthetic mixture of silica and magnesia having a surface area within the range of 40 to 200 m²/g, wherein the feed mixture contains the reactants in a mole ratio of $O_2/C_2H_4$ within the range of above 0.9 to 1.5, a mole ratio of $HCl/O_2$ within the range of 1.40 to 3.0 and a mole ratio of $HCl/C_2H_4$ within the range of 2.20 to 3.65 and the lower limit of the mole ratio of $HCl/O_2$ is correlated with the mole ratio of $O_2/C_2H_4$ to provide a maximum combustion rate in accordance with the following:

| Maximum Combustion Rate (Mole %) | 5 | 4 | 3 | 2 |
|---|---|---|---|---|
| $O_2/C_2H_4$ | 0.91 | 0.91 | 0.91 | 0.91 |
| $HCl/O_2 \geq$ | 2.20 | 2.27 | 2.38 | 2.58 |
| $O_2/C_2H_4$ | 1.10 | 1.10 | 1.10 | 1.10 |
| $HCl/O_2 \geq$ | 1.85 | 1.91 | 2.02 | 2.20 |
| $O_2/C_2H_4$ | 1.30 | 1.30 | 1.30 | 1.30 |
| $HCl/O_2 \geq$ | 1.55 | 1.60 | 1.69 | 1.86 |
| $O_2/C_2H_4$ | 1.50 | 1.50 | 1.50 | 1.50 |
| $HCl/O_2 \geq$ | 1.25 | 1.29 | 1.37 | 1.52 | and the upper limit of the mole ratio of $HCl/O_2$ is correlated with the mole ratio of $O_2/C_2H_4$ to provide an HCl conversion rate in accordance with the following:

| Conversion Rate of HCl (Mole %) | 80 | 90 | 92 | 94 | 96 |
|---|---|---|---|---|---|
| $O_2/C_2H_4$ | 0.91 | 0.91 | 0.91 | 0.91 | 0.91 |
| $HCl/O_2 \leq$ | 3.34 | 2.90 | 2.81 | 2.72 | 2.64 |
| $O_2/C_2H_4$ | 1.10 | 1.10 | 1.10 | 1.10 | 1.10 |
| $HCl/O_2 \leq$ | 2.95 | 2.56 | 2.48 | 2.40 | 2.32 |
| $O_2/C_2H_4$ | 1.30 | 1.30 | 1.30 | 1.30 | 1.30 |
| $HCl/O_2 \leq$ | 2.69 | 2.36 | 2.28 | 2.22 | 2.15 |
| $O_2/C_2H_4$ | 1.50 | 1.50 | 1.50 | 1.50 | 1.50 |
| $HCl/O_2 \leq$ | 2.43 | 2.15 | 2.09 | 2.04 | 1.98 |

16. A process for the oxychlorination of ethylene to produce a product which at least 15 mole percent of the ethylene is transformed into 1,1,2-trichloroethane and 1,1,2,2-tetrachloroethane, in which less than 5 mole percent of the ethylene is transformed into combustion products and in which less than 3 mole percent of the ethylene is transformed to unsaturated $C_2$ chlorinated compounds, comprising passing a gaseous feed mixture of ethylene, hydrogen chloride and an oxygen containing gas through a reaction zone maintained at a temperature within the range of 280° to 370° C and containing a fluid bed catalyst comprising a copper-containing catalyst deposited on a carrier consisting essentially of silica and magnesia having a surface area within the range of 10 to 200 m²/g, in which the molar feed ratios of the reactants are a ratio of $O_2/C_2H_4$ within the range of above 0.9 to 1.5, a ratio of $HCl/O_2$ within the range of 1.40 to 3.0 and a ratio of $HCl/C_2H_4$ within the range of 2.20 to 3.65.

17. A process for the oxychlorination of ethylene to produce a product in which at least 15 mole percent of the ethylene is transformed into 1,1,2-trichloroethane and 1,1,2,2-tetrachloroethane, in which less than 5 mole of the ethylene is transformed into combustion products and in which less than 3 mole percent of the ethylene is transformed to unsaturated $C_2$ chlorinated compounds, comprising passing a gaseous feed mixture of ethylene, hydrogen chloride and air through a reaction zone maintained at a temperature within the range of 280° to 370° C and containing a fluid bed catalyst comprising a copper-containing catalyst deposited on a carrier consisting essentially of silica and magnesia having a surface area within the range of 10 to 200 m²/g, wherein the feed mixture contains the reactants in a mole ratio of $O_2/C_2H_4$ within the range of above 0.9 to 1.5, a mole ratio of $HCl/O_2$ within the range of 1.40 to 3.0 and a mole ratio of $HCl/C_2H_4$ within the range of 2.20 to 3.65 and the lower limit of the mole ratio of $HCl/O_2$ is correlated with the mole ratio of $O_2/C_2H_4$ to provide a maximum combustion rate in accordance with the following:

| Maximum Combustion Rate (Mole %) | 5 | 4 | 3 | 2 |
|---|---|---|---|---|
| $O_2/C_2H_4$ | 0.91 | 0.91 | 0.91 | 0.91 |
| $HCl/O_2 \geq$ | 2.20 | 2.27 | 2.38 | 2.58 |

-continued

| Maximum Combustion Rate (Mole %) | 5 | 4 | 3 | 2 |
|---|---|---|---|---|
| $O_2/C_2H_4$ | 1.10 | 1.10 | 1.10 | 1.10 |
| $HCl/O_2 \geq$ | 1.85 | 1.91 | 2.02 | 2.20 |
| $O_2/C_2H_4$ | 1.30 | 1.30 | 1.30 | 1.30 |
| $HCl/O_2 \geq$ | 1.55 | 1.60 | 1.69 | 1.86 |
| $O_2/C_2H_4$ | 1.50 | 1.50 | 1.50 | 1.50 |
| $HCl/O_2 \geq$ | 1.25 | 1.29 | 1.37 | 1.52 | and the upper limit of the mole ratio of $HCl/O_2$ is correlated with the mole ratio of $O_2/C_2H_4$ to provide an HCl conversion rate in accordance with the following:

| Conversion Rate of HCl (Mole %) | 80 | 90 | 92 | 94 | 96 |
|---|---|---|---|---|---|
| $O_2/C_2H_4$ | 0.91 | 0.91 | 0.91 | 0.91 | 0.91 |
| $HCl/O_2 \leq$ | 3.34 | 2.90 | 2.81 | 2.72 | 2.64 |
| $O_2/C_2H_4$ | 1.10 | 1.10 | 1.10 | 1.10 | 1.10 |
| $HCl/O_2 \leq$ | 2.95 | 2.56 | 2.48 | 2.40 | 2.32 |
| $O_2/C_2H_4$ | 1.30 | 1.30 | 1.30 | 1.30 | 1.30 |
| $HCl/O_2 \leq$ | 2.69 | 2.36 | 2.28 | 2.22 | 2.15 |
| $O_2/C_2H_4$ | 1.50 | 1.50 | 1.50 | 1.50 | 1.50 |
| $HCl/O_2 \leq$ | 2.43 | 2.15 | 2.09 | 2.04 | 1.98 |

* * * * *